United States Patent
Connor

(10) Patent No.: US 11,262,590 B2
(45) Date of Patent: Mar. 1, 2022

(54) VIDEO GENERATION METHOD AND APPARATUS

(71) Applicant: Sony Interactive Entertainment Inc., Tokyo (JP)

(72) Inventor: Patrick John Connor, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 16/636,441

(22) PCT Filed: Jul. 13, 2018

(86) PCT No.: PCT/GB2018/052003
§ 371 (c)(1),
(2) Date: Feb. 4, 2020

(87) PCT Pub. No.: WO2019/030468
PCT Pub. Date: Feb. 14, 2019

(65) Prior Publication Data
US 2020/0175751 A1 Jun. 4, 2020

(30) Foreign Application Priority Data

Aug. 8, 2017 (GB) ........................................ 1712690
Oct. 11, 2017 (GB) ........................................ 1716621

(51) Int. Cl.
*G06F 3/01* (2006.01)
*G06K 9/32* (2006.01)
(Continued)

(52) U.S. Cl.
CPC ...... *G02B 27/0179* (2013.01); *A61B 5/02438* (2013.01); *A61B 5/0531* (2013.01);
(Continued)

(58) Field of Classification Search
CPC ............ G02B 27/0179; G02B 27/0093; H04N 13/268; H04N 13/25; H04N 13/275;
(Continued)

(56) References Cited

U.S. PATENT DOCUMENTS

2003/0193496 A1 10/2003 Wada
2005/0076060 A1* 4/2005 Finn ...................... G16H 40/20
(Continued)

FOREIGN PATENT DOCUMENTS

EP 2919098 A1 9/2015
EP 3035681 A1 6/2016
(Continued)

OTHER PUBLICATIONS

International Search Report and Written Opinion for corresponding PCT Application No. PCT/GB2018/052003, 14 pages, dated Aug. 23, 2018.
(Continued)

*Primary Examiner* — Grace Q Li
(74) *Attorney, Agent, or Firm* — Matthew B. Dernier, Esq.

(57) ABSTRACT

An image generation system includes a region of interest identifying unit operable to identify a region of interest within a piece of content, the piece of content comprising one or more objects, and an image generation unit operable to generate an image for display comprising one or more of
(Continued)

the one or more objects such that objects at a different visual depth to the region of interest are present in the generated image at a lower quality.

11 Claims, 13 Drawing Sheets

(51) Int. Cl.
| | |
|---|---|
| *G06T 15/04* | (2011.01) |
| *G06T 15/20* | (2011.01) |
| *G02B 27/01* | (2006.01) |
| *A61B 5/024* | (2006.01) |
| *A61B 5/0531* | (2021.01) |
| *A61B 5/00* | (2006.01) |
| *G02B 27/00* | (2006.01) |
| *H04N 13/268* | (2018.01) |
| *H04N 13/25* | (2018.01) |
| *H04N 13/275* | (2018.01) |

(52) U.S. Cl.
CPC ........ *A61B 5/6803* (2013.01); *G02B 27/0093* (2013.01); *G02B 27/0172* (2013.01); *G06F 3/013* (2013.01); *G06F 3/015* (2013.01); *G06K 9/3233* (2013.01); *G06T 15/04* (2013.01); *G06T 15/205* (2013.01); *H04N 13/25* (2018.05); *H04N 13/268* (2018.05); *H04N 13/275* (2018.05); *G02B 2027/0178* (2013.01); *G02B 2027/0187* (2013.01)

(58) Field of Classification Search
CPC ....... H04N 13/383; G06F 3/013; G06T 15/04; G06T 15/205; A61B 5/6803
See application file for complete search history.

(56) References Cited

U.S. PATENT DOCUMENTS

| | | | |
|---|---|---|---|
| 2013/0011063 A1 | 1/2013 | Kwon | |
| 2014/0267396 A1 | 9/2014 | Doolittle | |
| 2015/0260474 A1 | 9/2015 | Rublowsky | |
| 2015/0304623 A1* | 10/2015 | Yoon | H04N 13/361 |
| | | | 345/419 |
| 2016/0112727 A1* | 4/2016 | Mate | H04N 21/2353 |
| | | | 725/32 |
| 2016/0007016 A1 | 7/2016 | Holliman | |
| 2017/0004648 A1 | 1/2017 | Li | |
| 2017/0200302 A1* | 7/2017 | Haveman | G06T 15/80 |
| 2017/0316600 A1* | 11/2017 | Jeong | G06T 3/0062 |
| 2018/0160160 A1* | 6/2018 | Swaminathan | H04N 21/8456 |
| 2019/0155033 A1* | 5/2019 | Gelman | G02B 27/0172 |

FOREIGN PATENT DOCUMENTS

| | | |
|---|---|---|
| JP | 1161814 A | 6/1999 |
| JP | 2004005452 A | 1/2004 |
| JP | 2017021824 A | 1/2017 |
| WO | 2015128634 A1 | 9/2015 |
| WO | 2017025487 A1 | 2/2017 |

OTHER PUBLICATIONS

Combined Search and Examination Report for corresponding GB Application No. GB1716621.6, 2 pages, dated Apr. 12, 2018.
Notification of Reasons for Refusal for corresponding JP Application No. 2020-505429, 6 pages, dated Jan. 18, 2022.

* cited by examiner

| Object ID | Mesh 1 | Mesh 2 | Mesh 3 | Texture 1 | Texture 2 | Texture 3 | Metadata |
|---|---|---|---|---|---|---|---|

FIG. 8

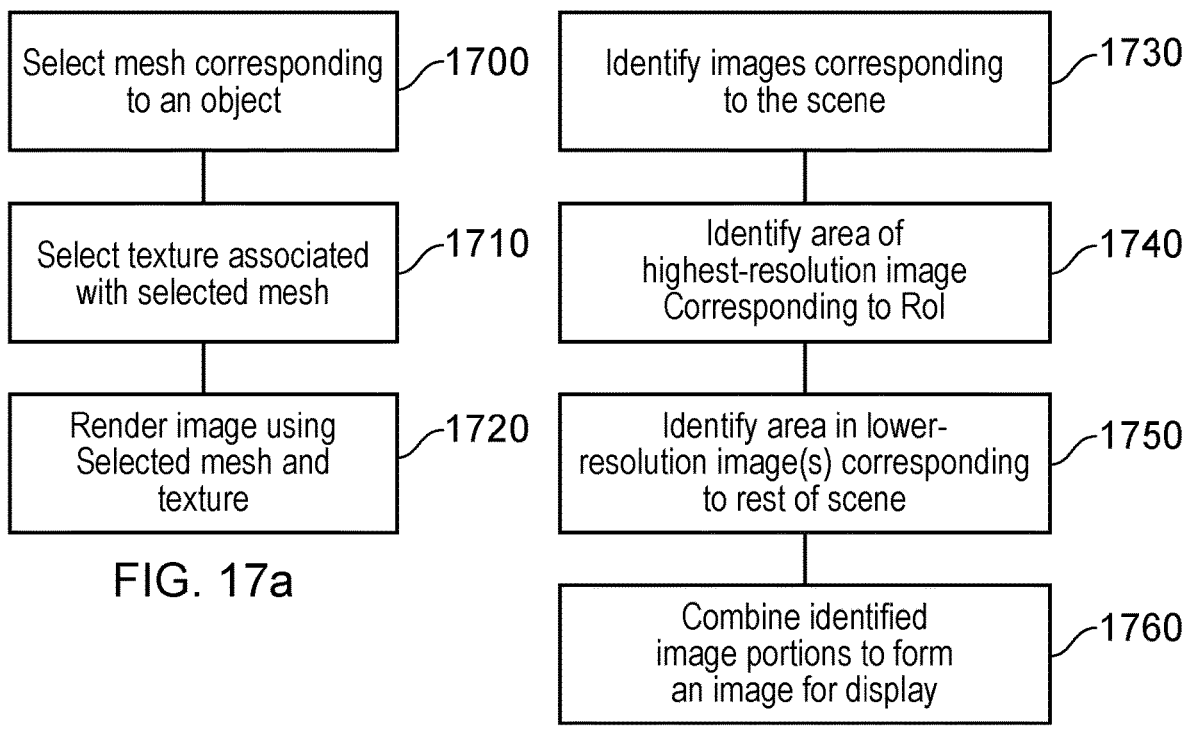

VIDEO GENERATION METHOD AND APPARATUS

BACKGROUND

This invention relates to a video generation method and apparatus.

The use of 3D image and video content has become more common in recent years, at least in part as a result of the development of more affordable display systems for personal use; for example, head-mountable display devices (HMDs) and 3D televisions.

3D content is generally provided with the aim of allowing a viewer to experience a greater sense of immersion, which may increase the viewer's enjoyment of the content. For example, a game that is presented in 3D (such as a virtual reality, VR, experience) may allow a player to feel as if they are present in the game environment. The addition of peripherals that enable a user to mimic real-world interactions more closely when providing inputs to the game may further enhance this experience.

In many cases, the level of immersion experienced by a viewer may be tied to how 'life-like' the presented scene appears. This leads to the use of high-quality display elements with a large field of view, such that the user is able to view content at a higher resolution and without other objects being visible (such as the straps on an HMD) to distract from the image. However, a problem with providing higher-resolution content is in that the file size of the content may be increased to an unusable level—storage and transmission of such content may no longer be viable or practical.

It is therefore desirable to improve the efficiency with which the content is stored; a more efficient storage allows for more image data to be stored without an increase in file size. An efficient storage therefore allows higher-resolution content to be produced without increasing the storage or transmission burdens on a system. Therefore a higher-resolution image may be provided using the same amount of data as a lower-resolution image that is stored inefficiently.

SUMMARY

The present disclosure is provided in the context of providing an arrangement in which an immersive viewing experience is improved for a viewer.

Various aspects and features of the present invention are defined in the appended claims and within the text of the accompanying description and include at least a display and a method of operating a display, as well as a computer program.

BRIEF DESCRIPTION OF THE DRAWING

Embodiments of the invention will now be described, by way of example only, with reference to the accompanying drawings, in which:

FIG. 8 schematically illustrates a data storage format;

FIGS. 17a and 17b schematically illustrate image generation methods.

DETAILED DESCRIPTION

Much of the following description uses the example of providing content using an HMD; however this should not be regarded as being limiting. The techniques described within may be equally applied to other display devices, such as 3D televisions, which are operable to display 3D content.

Figure 1:
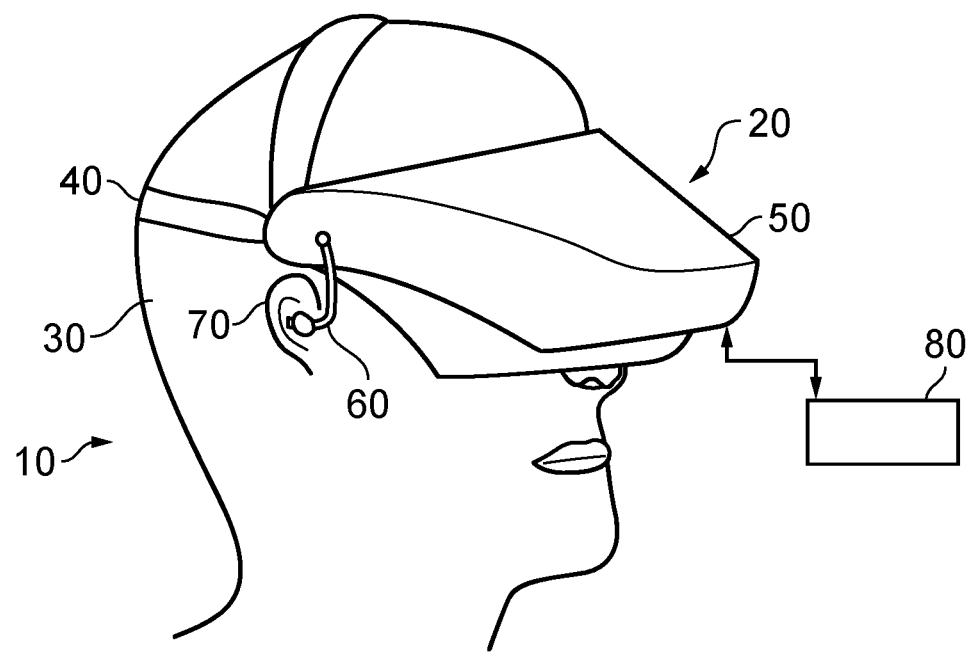
FIG. 1 schematically illustrates a user wearing an HMD.

Referring now to FIG. 1, a user 10 is wearing an HMD 20 on the user's head 30. The HMD comprises a frame 40, in this example formed of a rear strap and a top strap, and a display portion 50.

The HMD of FIG. 1 completely obscures the user's view of the surrounding environment. All that the user can see is the pair of images displayed within the HMD.

The HMD has associated headphone earpieces 60 which fit into the user's left and right ears 70. The earpieces 60 replay an audio signal provided from an external source, which may be the same as the video signal source which provides the video signal for display to the user's eyes.

In operation, a video signal is provided for display by the HMD. This could be provided by an external video signal source 80 such as a video games machine or data processing apparatus (such as a personal computer), in which case the signals could be transmitted to the HMD by a wired or a wireless connection. Examples of suitable wireless connections include Bluetooth (R) connections. Audio signals for the earpieces 60 can be carried by the same connection. Similarly, any control signals passed from the HMD to the video (audio) signal source may be carried by the same connection.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other examples, the user's view of the external environment may not in fact be entirely obscured; the displayed images could be arranged so as to be superposed (from the user's point of view) over the external environment.

Figure 2:
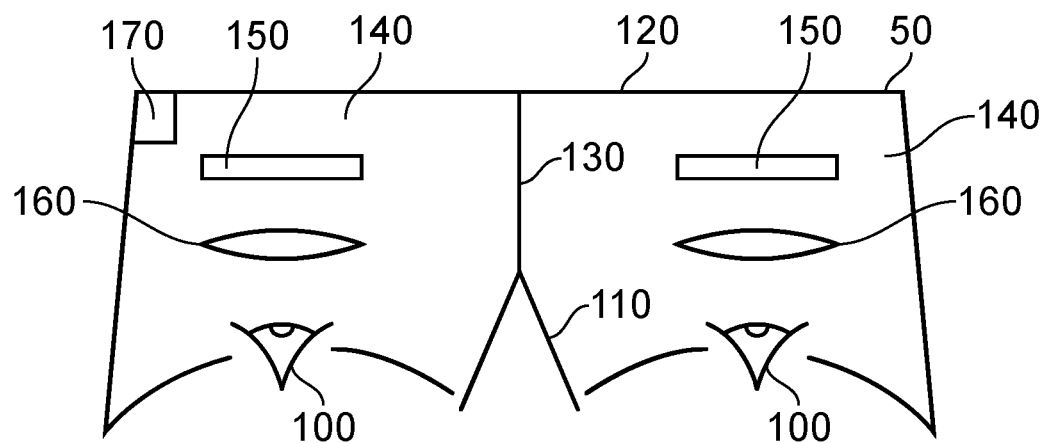
FIG. 2 schematically illustrates an internal view of an HMD.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160.

One or more imaging elements 170 may be provided within the HMD so as to enable images to be captured of one or both of the user's eyes. This may be useful for eye or gaze tracking, so as to identify a point of attention or object of interest of a user within a displayed image. In particular, the imaging element 170 may be a camera that uses visible or infra-red light to resolve an image of the HMD user's eye or eyes.

Figure 3:
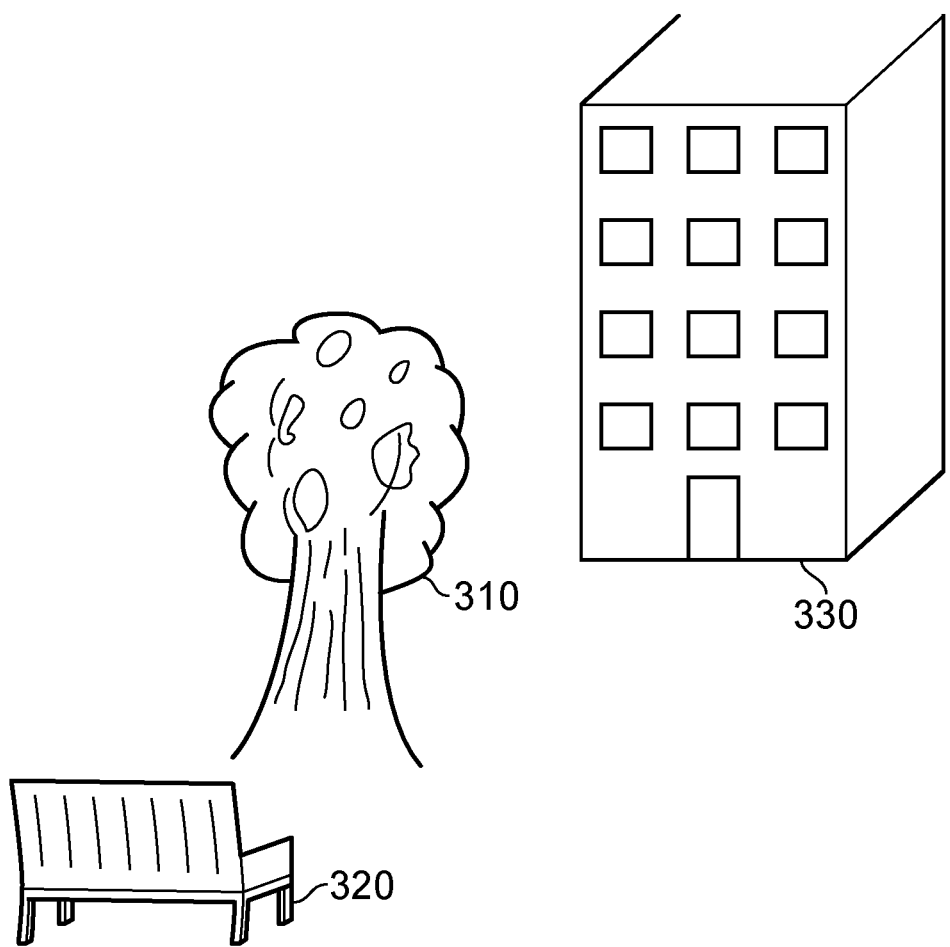
FIG. 3 schematically illustrates a virtual scene.

FIG. 3 schematically illustrates a virtual scene 300 that may be displayed to a viewer using the HMD. The virtual scene 300 comprises a tree 310, a bench 320 and a building 330. The bench 320 is located in the foreground, the tree 310 in the middle-ground and the building 330 in the background of the virtual scene 300; this means that when a viewer is presented with an image of the virtual scene the bench 320 will appear closest to the user, and the building 330 the farthest away.

When viewing such a virtual scene 300, the user will be focused on a specific image element at a particular depth within the displayed image at any given time; this may be an object of particular interest, for example. In this description, the word 'focused' is used to indicate that the user has turned their attention to a particular element in an image, rather than referring to the optical meaning of the word to imply that the user has their vision focused at a particular point. Indeed, the user may not be able to focus on a particular object as such, as the user instead views objects on the display rather than focusing on elements at particular depths.

The portion of the image upon which the user is focused will be referred to in this description as the point of attention. This corresponds to a region of interest in the virtual scene; for example, the point of attention could be the bottom left of a displayed image, which corresponds to a region of interest at the location of the bench. The region of interest may be defined to be an object, or an area or volume within the virtual scene.

As a result of the user focusing on the point of attention, the other objects in the image may not be closely viewed by the user; outside of the area upon which the user is focused the user is often unable to make out finer details of objects. In view of this, to reproduce these elements with a high resolution may be considered to be an inefficient use of resources (such as in processing and transmission of the image for display). It is therefore considered advantageous to provide an image in which image areas upon which the user is not focused (image areas other than the point of attention) have a lower resolution than those image areas corresponding to the point of attention.

When referencing the virtual scene 300 in this disclosure, it is assumed that the bench 320 is the region of interest for a particular viewer. The bench 320 may be identified as the region of interest in any suitable way, and as such the method of identification may be selected freely by the skilled person. In some examples, gaze tracking may be used (using the imaging element 170, for example) in order to determine where the user is looking at in real time and to what this corresponds to in the displayed images. This is an example of the region of interest being identified in dependence upon a detected point of attention of the user, the point of attention being obtained using eye tracking.

Figure 4:
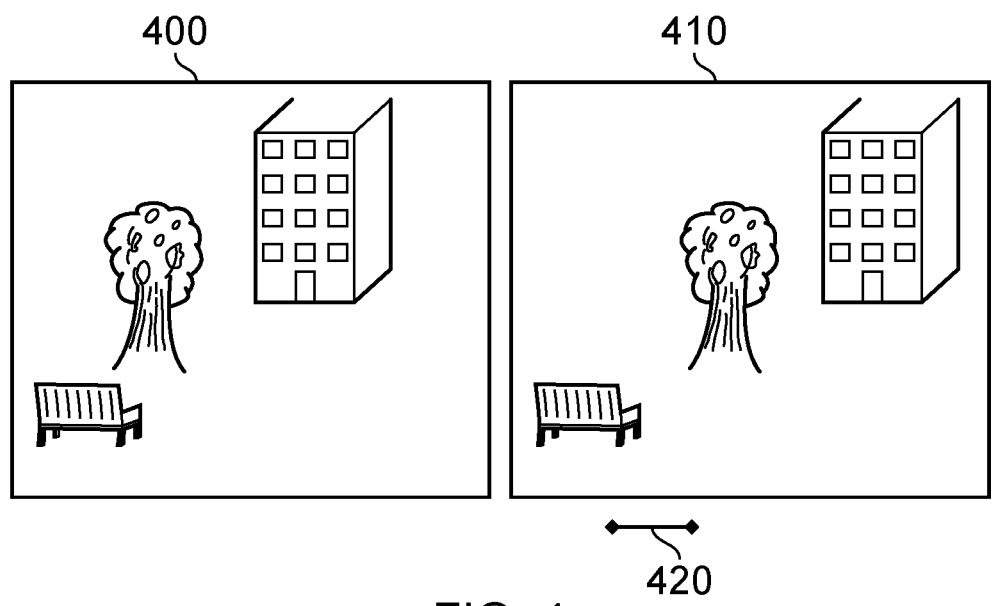
FIG. 4 schematically illustrates a stereoscopic image pair.

FIG. 4 schematically illustrates a pair of stereoscopic images corresponding to FIG. 3, the pair comprising a left image 400 and a right image 410. The bench 320 is displayed at the same position in each of the images, whilst the tree 310 and building 330 are displayed at different positions within each image. For example, the tree 310 in the left image 400 and the right image 410 are separated by a disparity distance 420. These varying disparities create the sense of depth that is experienced by a user upon viewing the content.

When focused on a particular object, the user's eyes adopt a position according to the disparity between the left and right images for that object. This may cause the other objects within the image to be displayed incorrectly, as the required eye positions for correct viewing are different. Therefore the left and right components of the image may not overlap correctly, resulting in an incorrect viewing of the image by the user.

Determining the region of interest in a virtual scene may be performed in a number of different ways. In some examples, gaze tracking may be used (using the imaging element 170, for example) in order to determine where the user is looking at in real time and to what this corresponds to in the displayed images. This is an example of the region of interest being identified in dependence upon a detected point of attention of the user, the point of attention being obtained using eye tracking.

Alternatively, or in addition, an expected region of interest may be determined by aggregating gaze information (either during production of content, or after release, or both) from a plurality of users so as to identify the most interesting elements (and thus regions of most general interest) in advance of a particular viewer's playback of the content. For example, gaze detection information from a plurality of users could be monitored so as to identify one or more regions in a virtual scene or image frame (or any other portion of content) that may qualify as a region of interest. This information may be provided as metadata in the content, or be able to be acquired separately to the content such as via a download from the internet.

Alternatively, or in addition, regions of interest may be identified using contextual information for the content; in this particular example, the bench 320 may have particularly interesting features and thus be expected to draw the viewer's attention more than the tree 310 or building 330. Similarly, regions or objects of interest may be derived from the user's interaction with the content. For example, if a user is fighting an enemy in a game then it is expected that the user is going to be focused on that enemy rather than any background elements within the virtual scene. In the context of video content being displayed, contextual information could indicate an important object, character or event upon which the user's focus is likely to be drawn to, such as a football in a football match or an actor who is currently speaking in a particular scene of a movie.

A region of interest has generally been described here as a particular object; however in some embodiments it may be a group of objects or a particular volume of space within a virtual scene. For example, if a pair of people were sitting on the bench 320 then the region of interest could be defined as being the three 'objects' together—that is, the bench 320 and each of the two people. Alternatively, the region of interest could be defined as a volume that envelops the bench 320 and the people. The volume may be defined to be any suitable size; for example, the volume may be defined as the smallest possible size including the objects of interest, so as to reduce the size of the high-quality portions of the image, or as a size that allows for a suitable amount of motion of the objects or for surrounding context to be included in the high-quality area.

Figure 5:
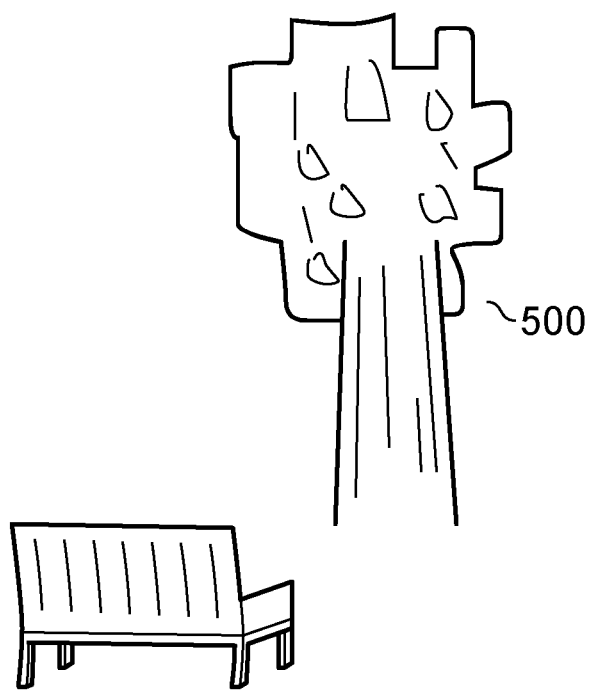
FIG. 5 schematically illustrates a low-quality mesh.
Figure 6:
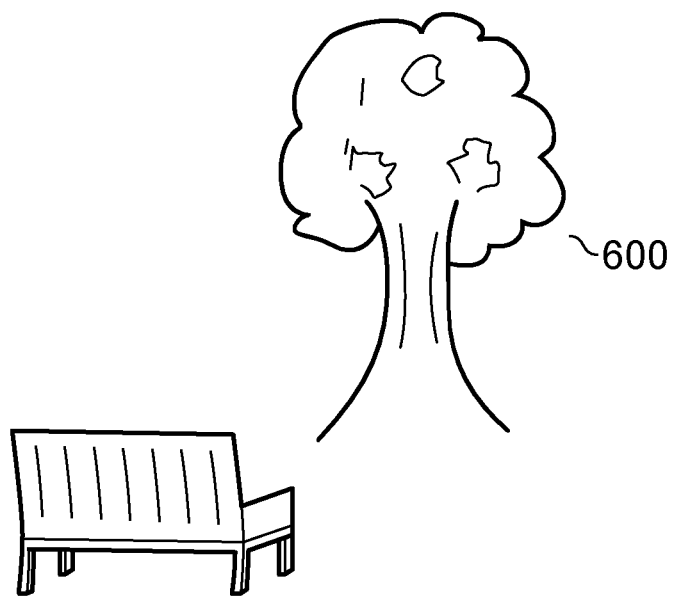
FIG. 6 schematically illustrates a low-quality texture.

FIGS. 5 and 6 schematically illustrate examples of the display of objects other than that upon which the user is focused being different to that of the object upon which the user is focused. In this example, it is considered that the user is focusing on the bench 320 in the foreground of the virtual scene, and thus the portion of the image corresponding to the bench 320 is considered to be the point of attention. A different low-quality representation of the tree 310 is provided in each of these Figures, while the building 330 is not represented in this image.

In some embodiments, it may be the case that the building 330 is not present in the displayed image as it is at a depth too far from the point of attention of the user (in effect, the depth separation between the bench 320 and the building 330 may be over a particular threshold value). However, in other embodiments a low-quality representation is provided even when the depth difference is large as it is in the present example. Whether or not an object is displayed in such a situation may be determined freely, for example in dependence upon the importance of the object in the context of the content being viewed.

In some embodiments the quality at which an object is displayed is dependent upon only the object and its depth separation from the region of interest. However, it is also considered that the quality at which one or more other objects in the image to be generated are to be displayed is dependent upon a relationship between the one or more other objects and the object that is the region of interest.

One example of this is that of a user focusing on or holding/interacting with a key; it may be advantageous to display a corresponding lock and/or door at a higher image quality than the depth separation would usually suggest. This may be advantageous both in anticipating the user's change of focus in the image (as the user is likely to seek the door once seeing the key), and ensuring that it is recognisable even the viewer is not directly focusing on the object (while not so relevant for a door, in some examples a low-resolution representation of an object may not be as easy to identify as a high-resolution representation).

The image quality can be represented by an image resolution (for example a lower resolution corresponding to a lower quality), and/or by a resolution of texture mapping (for example, texture polygon size being larger for a lower quality), and/or by other different image parameters such as a smaller colour palette corresponding to a lower quality image region. However, in example embodiments, the quality is dependent upon a respective image texture as discussed below. The low-quality representation may be provided by using a different quality of texture to be applied to a mesh representing the tree 310, for example. Alternatively, or in addition, different meshes may be used to represent the object at different qualities. Alternatively, or in addition, an image for display may be generated by combining areas of different pre-generated images at different qualities.

In FIG. 5, the low-quality representation 500 approximates the shape of the tree 310 with a lower-quality mesh. The use of the lower-quality mesh means that the displayed image may be blockier and/or worse representations of the intended shape. It may be advantageous that the user is unable to tell the difference between the two shapes without focusing on the low-quality representation 500 specifically; in this Figure the differences between the two representations are exaggerated for clarity. If a suitably similar mesh is selected to replace the use of the higher-quality representation of the object, the user may find the use of a substitution undetectable in normal viewing.

In FIG. 6, the low-quality representation 600 approximates the display of the tree 310 using the same higher-quality mesh but with a lower-quality texture applied to it. This is shown by the use of less detail on the trunk of the tree 310, and the lower-resolution of the leaves/branches that appear within the boundary of the tree 310. A texture may be considered to be of a lower quality if it possesses any one or more of the following indicators of lower quality: the texture is of a lower resolution than alternative textures, uses a reduced colour palette, uses less shading and/or less complex shaders. This list is exemplary, rather than exhaustive, and a lower quality texture may alternatively or additionally be identified by any number of other indicators. A viewer, upon viewing objects possessing one or more of these indicators, would generally regard the display of the object as an inferior representation of the object.

Figure 7:
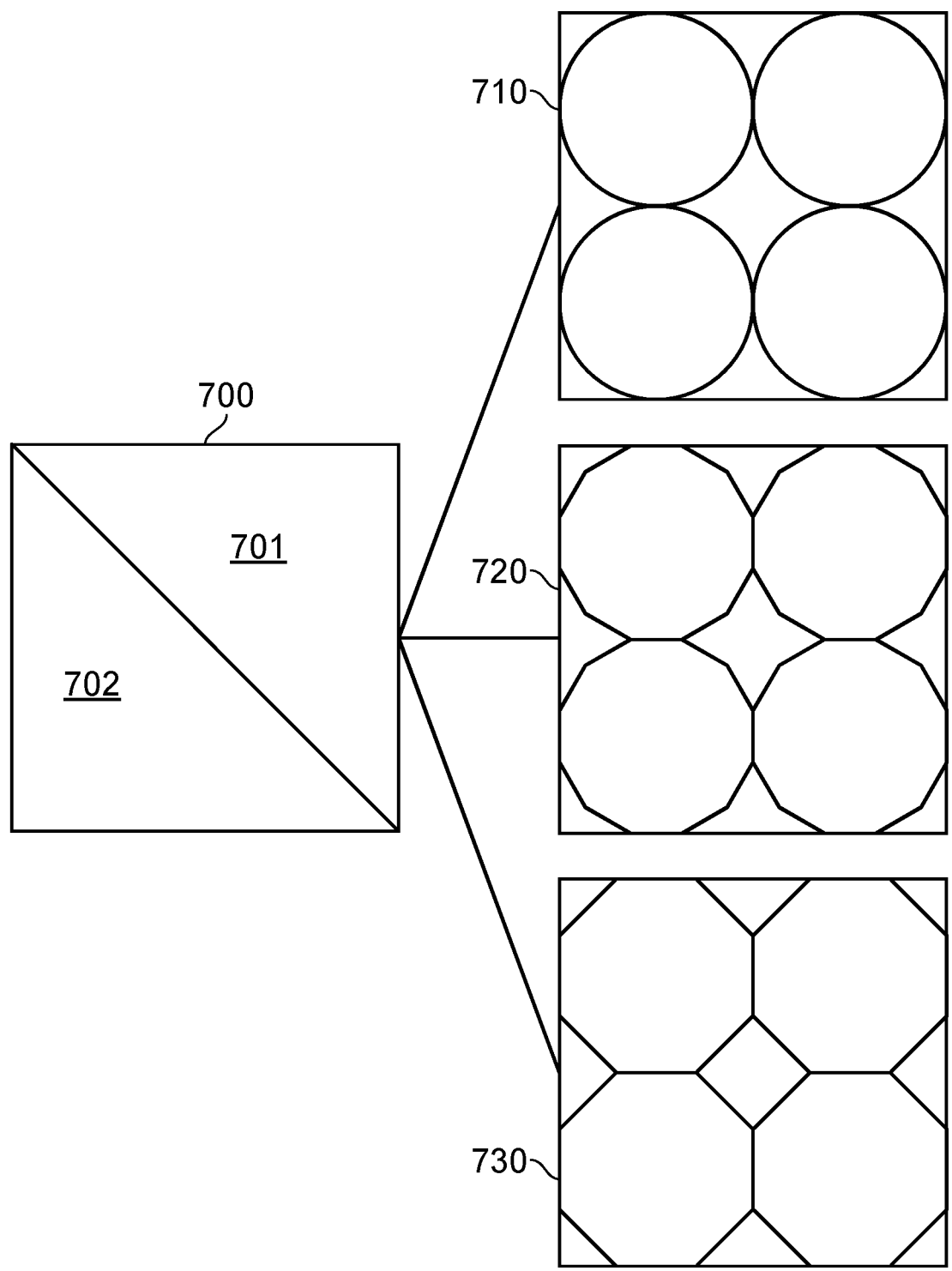
FIG. 7 schematically illustrates a mesh and textures.

FIG. 7 schematically illustrates a plurality of textures 710, 720, 730 corresponding to a mesh 700 comprised of polygons 701 and 702. A polygon is a basic shape (such as a triangle) that is used to build up a representation of a complex object in a simplified manner; this representation is referred to as a mesh. In order to arrive at a more visually accurate representation of an object, a texture may be applied to the mesh so as to apply colours and the like to each of the polygons.

In general, a mesh would comprise a larger number of polygons than the mesh 700 so as to be able to represent a more complex shape. For example, a mesh may be used to represent the tree 320. The textures 710, 720, 730 are shown with simple shapes for clarity; however a texture could be more complex and comprise much more detailed imagery. In the example of the tree 320, the textures may include details such as leaves that are applied to the mesh representing the general tree shape.

Texture 710 is the highest resolution of the three textures, whilst texture 730 is the lowest resolution and texture 720 is of an intermediate resolution. The differing resolution of the textures is intended to illustrate a varying texture quality, although the quality could of course vary in other ways—such as the range of colours or the level or type of shading that is applied. The difference in resolutions of the textures in this Figure is illustrated by using straight lines in the textures 720 and 730 to approximate the circles in the texture 710.

To provide examples in the context of applying textures to a tree-shaped mesh, an example of the differences in display caused by using each texture is provided.

A high-quality texture (such as the texture 710) in this example may comprise a large number of well-defined leaves, each with clear details such as colouring or surface texturing. For example, leaves may have more than one colour and the leaves may each be coloured differently; this is useful for representing a tree in autumn, when the colours are more varied. Fruit or birds or the like that can add character to the tree may also be shown in the texture, provided that they are not represented by their own respective meshes and textures.

A medium-quality texture (such as the texture 720) in this example may comprise leaves that only approximate the shapes in the high-quality texture. In addition, the range of colours used to represent the leaves may be reduced so as to utilise a smaller colour palette, and a smaller number of different leaf colourings may be used (such that the number of unique leaves is reduced). The surface texturing may still be provided, but in a less detailed manner—for example, the same surface texture may be applied to the whole tree rather than each individual leaf in the texture.

A low-quality texture (such as the texture 730) in this example may comprise fewer, larger leaves with shapes that approximate those of the higher-quality textures. The leaves may each have the same colour, and any additional details such as fruit may be omitted. Surface texturing may be omitted entirely, or only a very basic model applied.

Three textures are shown in FIG. 7, but of course any number of different quality textures could be selected from in order to provide the desired level of quality. The texture that is selected for use with an object may be dependent upon the depth separation between the point of focus of a viewer and the object to which the texture is applied, or any other suitable measure. User preferences may also considered when determining which texture to apply to an object, such as to define the relationship between the lowering of quality and the distance in a depth direction so as to cause a more or less sharp gradient of decreasing quality.

In some embodiments it is expected that the quality at which an object is displayed decreases with increasing depth difference from the region (or object) of interest. This may be a linear decrease such that the resolution used to display an object halves as the distance from the region of interest doubles, for example, or any other relationship. Exceptions to this may be present in images, such as for particularly important objects which would not be appropriate for display at a lower image quality. This is not essential, however, as the same quality level could be applied to all objects outside of the region of interest.

In some embodiments, the mesh used to represent a particular object may also be varied. For example, a lower-quality mesh could be selected for an object that is not the object of interest; such a mesh may be blockier and less similar to the actual shape of the object it is used to represent. Each quality of mesh that is available may also be associated with one or more textures of varying qualities so as to provide a greater range of possible display qualities for objects in the image. For example, three meshes could be provided and each could be associated with three textures so as to provide nine different quality levels for each object. Alternatively, it may be possible to apply (with a mapping or the like to account for differences in shape) the same texture to any of the meshes associated with the object.

Of course, it would be appreciated that it is not essential that each object has the same number of corresponding textures and/or meshes in such embodiments. For example, particularly important objects in a virtual scene (as determined based on user preference or in-content context or the like) may have a greater number of corresponding textures and/or meshes so as to provide a more gradual decrease in display quality. This is less important for less important objects, for which even only two associated textures may be used in a binary 'object-of-interest' or 'not-object-of-interest' display method.

FIG. 8 schematically illustrates a file format for storing associated mesh and texture information. Such a file may be provided for each object in a virtual scene, or each unique object if objects may appear more than once in an image.

This file format comprises a header that identifies the object that is represented by the meshes and textures; this may be in the format of an object ID or a description of the type of object for example.

Mesh 1, mesh 2 and mesh 3 are each meshes representing the same object, each mesh having a different quality (as described above). As noted above, a mesh is a model formed of a plurality of polygons to represent the shape and/or structure of an object in a simplified manner. Meshes generally lack any information about the appearance of the object, and as such meshes are generally not suitable for generating an image without applying a texture to the mesh.

Texture 1, texture 2 and texture 3 are each textures representing the same object, each texture having a different quality (as described above). These textures comprise information (such as colour and surface texture) that may be applied to a mesh so as to generate a complete model of an object. Each of these textures may be associated with a particular mesh (to ensure that the correct texture and mesh are paired in view of the meshes possibly having different shapes), or may only be associated with the object generally.

The metadata field may be used to store information relevant to the display of the object. For example, contextual information may be provided in this field so as to identify the importance of the object or the like. Alternatively, or in addition, information describing which texture to select at different depth differences from the region of interest may be provided.

While the above description relates to the generation of images for display from meshes and textures, any appropriate image generation method may be used. For example, in some embodiments the images may be generated by combining images of several different resolutions; this may be particularly useful when preparing pre-recorded video or image content for display, as mesh and texture information may not be readily available. In such an example, a high-resolution image may be used to represent the region of interest while low-resolution image portions may be combined with this to generate the image for display. For example, pre-generated images may be provided that each utilised one of the textures shown in FIG. 7 and instead of selecting a desired texture to apply to a mesh, a portion of an image generated with that mesh is extracted for use in the image-combining process.

Figure 9:
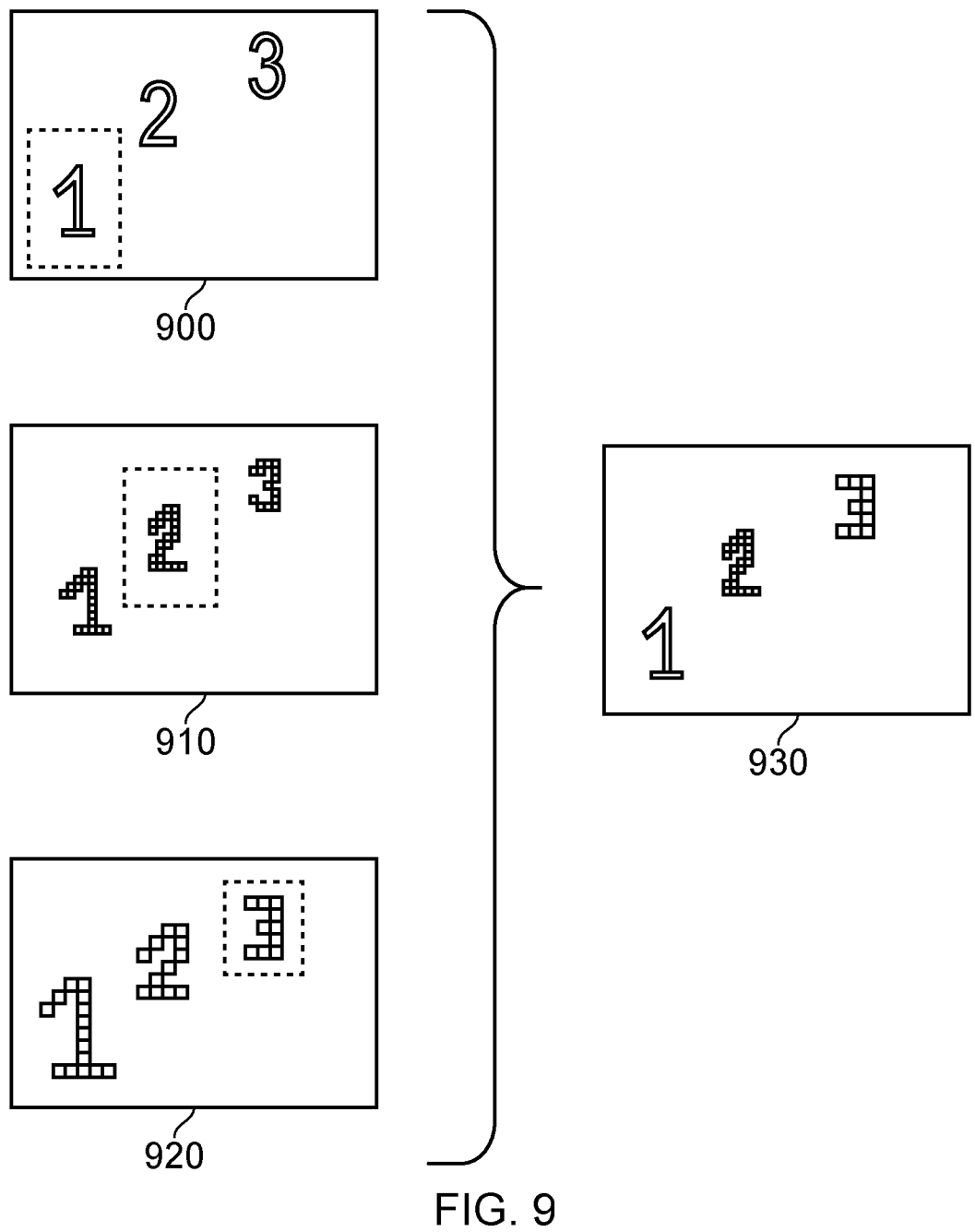
FIG. 9 schematically illustrates a plurality of pre-generated images of different resolutions.

FIG. 9 schematically illustrates a combination of images of different qualities in order to generate an image for display. Three pre-generated images are shown; a high-quality image 900, a medium-quality image 910 and a low-quality image 920. Each of these shows the numbers 1, 2 and 3 at different resolutions.

A composite image 930 is generated using an element from each of the images 900, 910 and 920. In this example, the region of interest is taken to be the '1', with the '2' being the closest in the depth direction and '3' being the furthest in the depth direction. As a result, the '1' is expected to be displayed at the highest quality, the '2' at a medium quality, and the '3' at the lowest quality.

In order to generate the expected image, the '1' is taken from the image 900, the '2' from the image 910 and the '3' from the image 920. These three elements are then combined into a single image.

The size of the area that is taken from each image may be selected freely; it may be advantageous to select only a small high-quality area so as to reduce the amount of data this is required to store the image for display, for example. Alternatively, selecting a larger area may be considered advantageous so as to ensure that the whole of the region of interest is displayed at a high quality.

Of course, more than three objects may be identified in an image for display, and therefore multiple image elements may be acquired from one or more of the pre-generated images.

The environment in which the objects are present in the image may be displayed at any appropriate image quality. In some examples, the environment is acquired from the lowest-quality image as it may be considered unlikely that the user will turn their attention to anything but the objects in the image. Alternatively, the quality of display used for the environment may be selected based on proximity to the objects; for example, a high quality image source may be used for the portion of the environment surrounding the '1' so as to ensure that the user is presented with a high quality image in that area.

In some embodiments it is considered that an image for display may be generated using a hybrid method such that a portion of the image is generated from pre-rendered content and a portion using mesh and texture data. For example, in a game setting, it may be advantageous that the environment and key objects (such as those present in every player's playthrough) are represented by pre-rendered images while user-created characters or other objects that are not the same for all players are generated using mesh and texture data.

Figure 10:
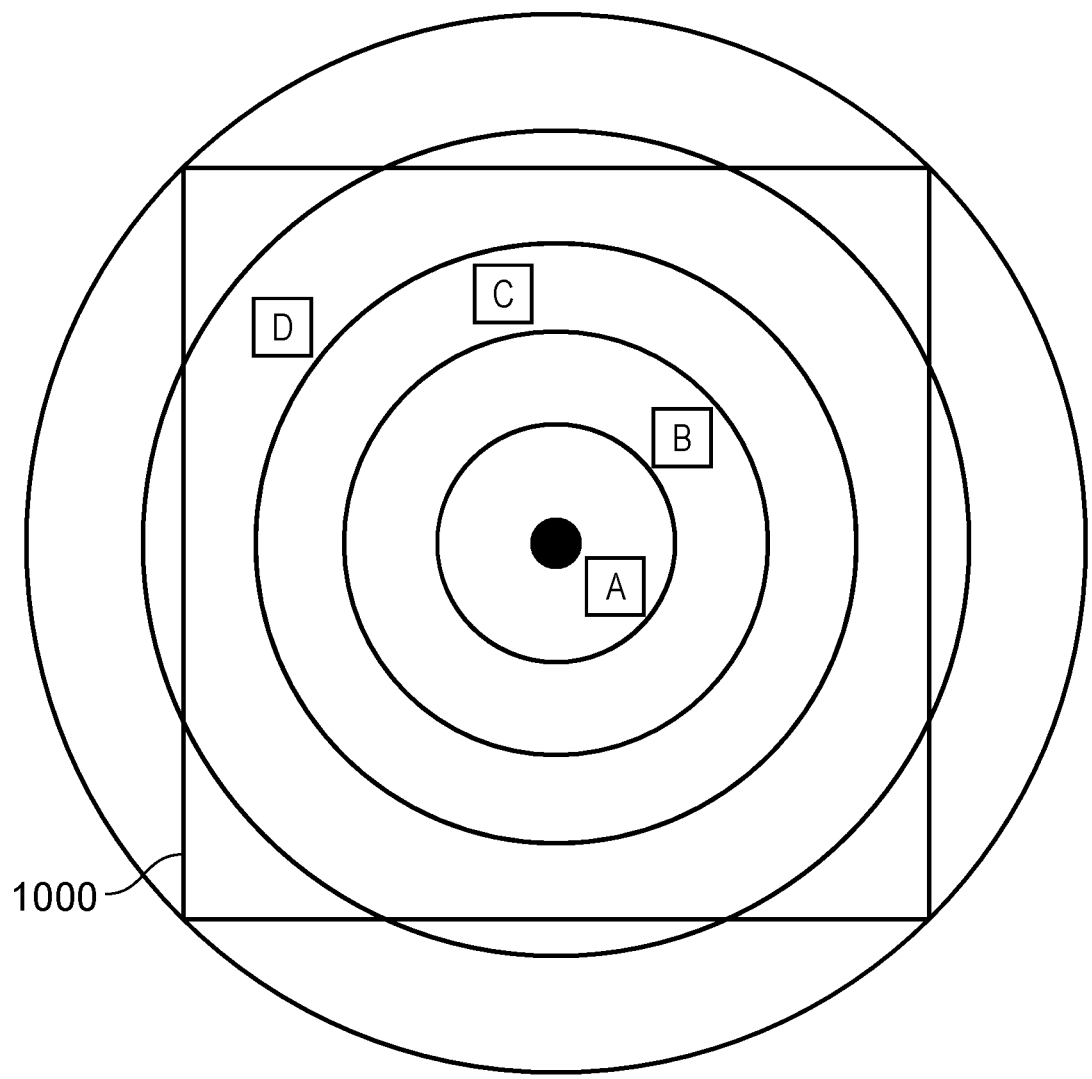
FIG. 10 schematically illustrates a plan view of a virtual scene.

FIG. 10 schematically illustrates a virtual scene comprising objects A, B, C and D in a room 1000. The concentric circles in this Figure are provided so as to divide the virtual scene into layers of different depths surrounding the viewer (represented by the dark circle in the centre). In some embodiments, a region of interest may be defined as a spherical or cylindrical shell (or indeed, a shell of any shape) that covers one of these layers. To relate this to FIGS. 3 and 9, object A could be the bench 320 or '1', object B could be the tree 310 or '2' and object C could be the building 330 or '3'.

In some embodiments, layers may be used to provide a discrete measure of the separation between objects in a virtual scene. For example, the depth difference between object A and object B may be defined as a single layer, while the depth difference between objects A and D may be defined as three layers. This information may be more useful when determining an appropriate quality of image to use for displaying an object, as a more precise measurement may be avoided. In some embodiments, objects may be provided with metadata that defines which layer they belong to, or alternatively this may be easily derivable given information about the position of the object in the virtual scene. Such a layer-based method may be advantageous as there is likely to be a relatively small number of available qualities at which an object may be rendered, and so fine-scale calculations may be unnecessary.

Considering an example in which object B is the region of interest, objects A and C may be displayed at the same image quality as the depth difference between objects A and B and objects B and C are similar (each one layer). Object D would be displayed with a lower quality than objects A or C, as it is further removed from object B in the depth direction (two layers, rather than one).

In some embodiments, objects A and C may be displayed differently as they are opposite sides of object B. While the magnitude of the depth difference may be the same, one is a positive separation and the other is negative. For example, it may be expected that a higher resolution is desirable for displaying object A than object C as it is nearer to the viewer and therefore it is more likely that a viewer would expect to be able to make out finer details on object A even when not focused on the object.

Figure 11:
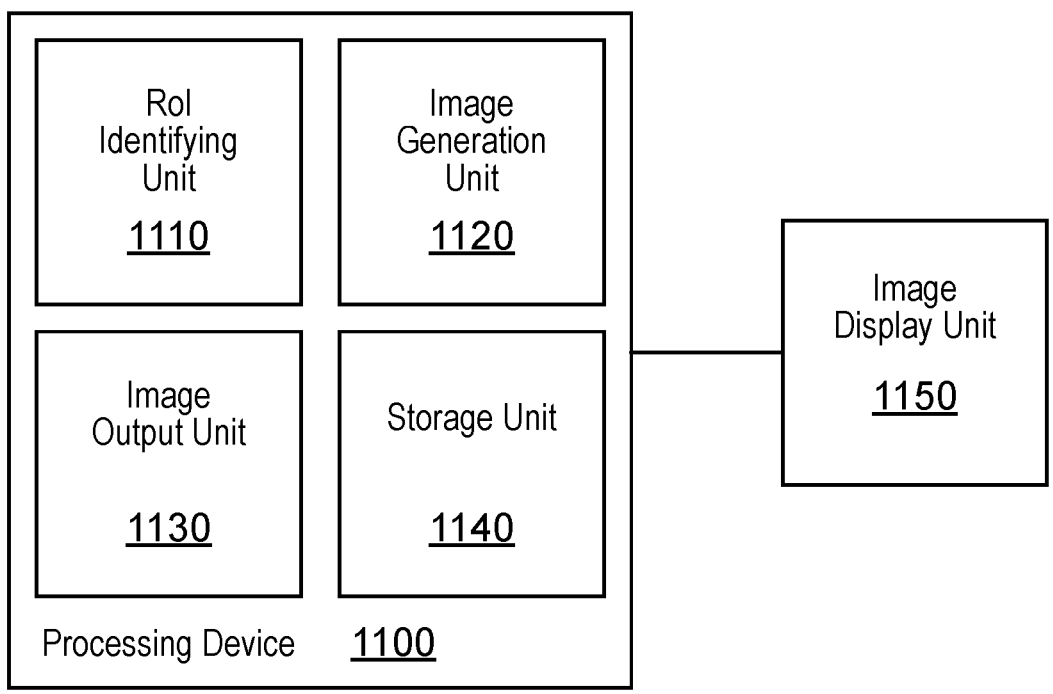
FIG. 11 schematically illustrates an image generation and display system.

FIG. 11 schematically illustrates an image generation system comprising a processing device 1100 and a display unit 1150. The processing device 1100 comprises a region of interest (RoI) identifying unit 1110, an image generation unit 1120, an image output unit 1130 and a storage unit 1140. The distribution of the different functional units shown in FIG. 11 is entirely exemplary, and the each of the functions could be performed at either unit. Alternatively, the image display unit 1150 may be provided as the same device as the processing device 1100.

The region of interest identifying unit 1110 is operable to identify a region of interest within a piece of content. The piece of content may be a game, film, or any other interactive or video content. As noted above, this identification may be based upon an analysis of the content to identify objects or areas of interest, or it may be based upon more user-based measures such as a gaze detection. The image generation unit may be operable to select one of a plurality of available textures corresponding to an object for display, the available textures each being of a different quality and/or resolution.

The image generation unit 1120 is operable to generate an image for display representing the piece of content comprising one or more of the one or more objects such that objects at a different visual depth to the region of interest are present in the generated image at a lower quality. Examples of displaying objects at a lower quality is that of displaying the objects with a lower image resolution, less texture detail, lower-resolution meshes, reduced shader quality, and using fewer unique textures for objects that are presented more than once in an image for display. The phrase 'visual depth' here is used to indicate that the objects are not at different depths, as they are all present on the display, but rather that they appear to be at different depths to the viewer of the content in which the objects are present.

The image output unit 1130 is operable to output the generated images to the image display unit 1160. In embodiments in which the image display unit 1150 is formed as a separate device, this output may be performed using any suitable wired or wireless connection.

The storage unit 1140 is operable to store information that is used for the generation of images by the image generation unit 1120. This may comprise a variety of mesh and texture information, for example, and/or image content at a plurality of different resolutions from which an image for display may be generated in dependence upon an identified region of interest.

The image display unit 1150 is operable to display the generated images to a viewer. In some embodiments the image display unit 1150 is an HMD associated with the processing device 1100. Alternatively, the image display unit 1150 may be a television or other display operable to display the generated image content. In either case, it is conceivable that the image display unit 1150 may provide some or all of the functionality described above with reference to the processing device 1100.

Figure 12:
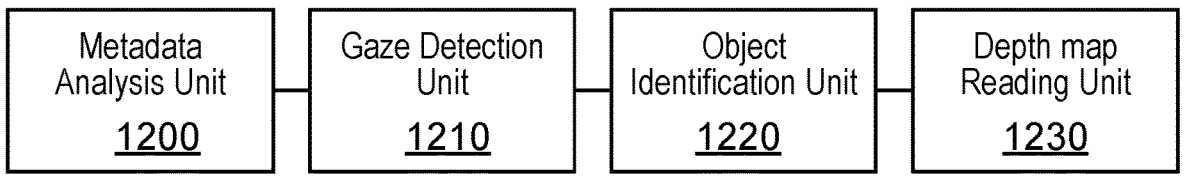
FIG. 12 schematically illustrates a region of interest identifying unit.

FIG. 12 schematically illustrates components of a region of interest identifying unit 1110. These include a metadata analysis unit 1200, a gaze detection unit 1220, an object identification unit 1220 and a depth map reading unit 1230.

The metadata analysis unit 1200 is operable to examine metadata associated with the content that describes a region of interest. For example, metadata associated with a movie (either provided with the video content, or obtained separately) may identify any important actors or objects in particular scenes that are likely to draw the user's attention. Therefore the region of interest identifying unit 1110 is operable, using the metadata analysis unit 1200, to identify a region of interest using contextual information for the content The gaze detection unit 1210 is operable to use information obtained from inwards-facing cameras, for example, in order to derive a point of attention for a user. This point of attention may be used to identify a region of interest in the content in a number of ways. It is therefore apparent that the region of interest identifying unit 1110 is operable to identify a region of interest using a detected point of attention of the user, the point of attention being obtained using eye tracking, by using the gaze detection unit 1210.

The object identification unit 1220 may use the point of attention information from the gaze detection unit 1210 in order to identify a particular object as being the region of interest. This may be performed using image analysis, for example, or by comparing the point of attention information with location information for objects within a virtual scene. This is an example of the region of interest identifying unit being operable to identify a region of interest as an object in the content.

The depth map reading unit 1230 may be used in conjunction with one or more of the gaze detection unit 1210 and the object identification unit 1220 to identify a region of interest. For example, a depth map may be used with the point of attention information to identify a volume or area in the virtual scene at a particular depth that may be considered to be the region of interest. Alternatively, or in addition, a depth map may be used to assist with object identification by the object identification unit 1220.

Figure 13A:
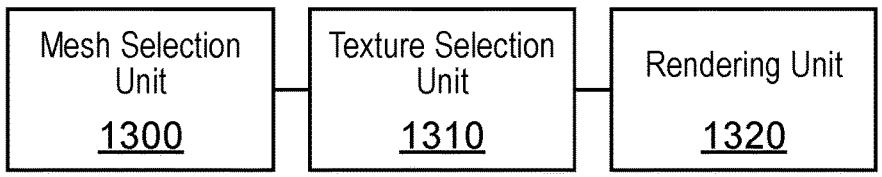
FIGS. 13a and 13b schematically illustrate image generation units.
Figure 13B:
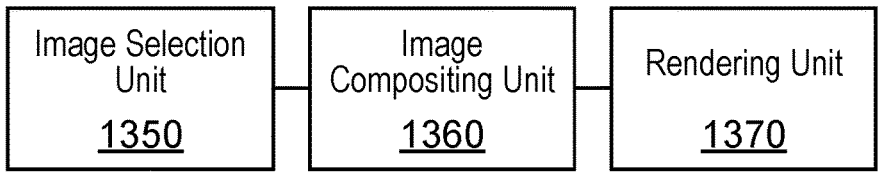

FIGS. 13*a* and 13*b* schematically illustrate two examples of an image generation unit 1120. While shown here as separate units, each could be provided as a part of a single image generation unit 1120. FIG. 13*a* shows a mesh selection unit 1300, a texture selection unit 1310 and a rendering unit 1320. FIG. 13*b* shows an image selection unit 1350, an image compositing unit 1360 and a rendering unit 1370.

The mesh selection unit 1300 is operable to select a mesh for each object from the one or more meshes that are available; for example, the mesh selection unit may select from mesh 1, mesh 2 or mesh 3 of the data structure of FIG. 8 in dependence upon the desired representation quality of the object to be displayed. The image generation unit 1120, by use of the mesh selection unit 1300, is therefore operable to select one of a plurality of available meshes for use in rendering an object for display, the available meshes each being of a different quality.

The texture selection unit 1310 is operable to select a texture corresponding to the meshes selected for each object by the mesh selection unit 1300. In some embodiments, any texture associated with the object may be selected. However in some embodiments, as noted above, the texture selection unit 1310 may only be able to select from a subset of textures for the object corresponding to the mesh that is selected by the mesh selection unit 1300.

The image generation unit 1120, by use of the texture selection unit 1310, is therefore operable to select one of a plurality of available textures for use in rendering an object for display, the available textures each being of a different quality. In some embodiments, the available textures corresponding to an object are each of a different resolution.

The rendering unit 1320 is operable to render an image for display using the selected mesh and texture information.

Turning now to FIG. 13*b*, the image selection unit 1350 is operable to select (based on the quality of representation that is desired) which objects should be acquired from each image. These images may be referred to as candidate images, as each is a candidate for use to represent a particular object in an image to be displayed. To use the example of FIG. 9, the image selection unit 1350 would be operable to identify that the '1' should be obtained from the image 900, the '2' from the image 910, and the '3' from the image 920.

The image compositing unit 1360 is operable to combine the selected image portions into an image for display; with respect to FIG. 9, this would comprise the generation of the image 930 from the component parts taken from images 900, 910 and 920 in line with the operation of the image selection unit 1350. The image generation unit 1120 is therefore operable to generate an image by combining areas from one or more candidate images of different qualities.

The rendering unit 1370 is operable to generate an image for display from the composite image generated by the image compositing unit 1360.

It is therefore apparent that the image generation unit is operable, using either the arrangement of FIG. 13*a*, FIG. 13*b*, or a combination of the two, to vary the quality of the one or more objects in the generated image such that the quality decreases with increasing depth difference from the region of interest. This may be achieved by selecting the quality of the representation in dependence upon the depth difference between the region of interest and the object as described in this application.

Figure 14:
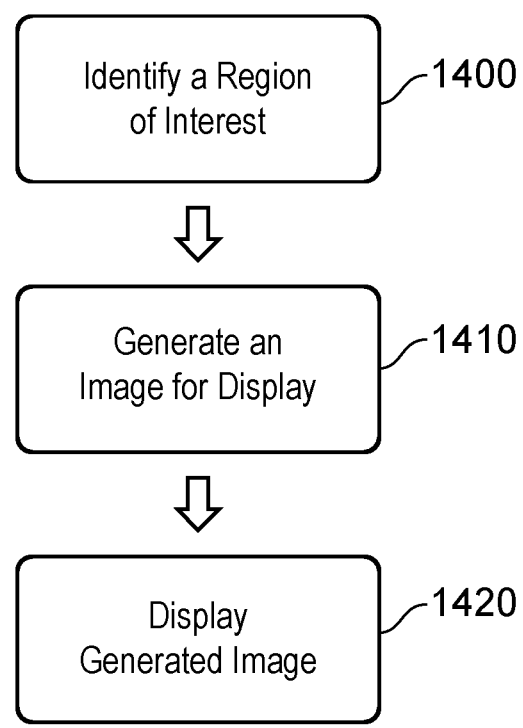
FIG. 14 schematically illustrates an image generation and display method.

FIG. 14 schematically illustrates an image generation method.

A step 1400 comprises identifying a region of interest within a piece of content, the piece of content comprising one or more objects. This step is discussed in more detail with reference to FIGS. 15*a*, 15*b* and 15*c*.

A step 1410 comprises generating an image representing the piece of content for display, wherein objects at a different depth to the region of interest within the content are displayed with a lower quality. This step is discussed in more detail with reference to FIGS. 17*a* and 17*b*.

A step 1420 comprises displaying the images generated for display to a viewer; it is not essential that this step is performed at the time of generating the image, as the images for display may be generated for later playback.

Figure 15A:
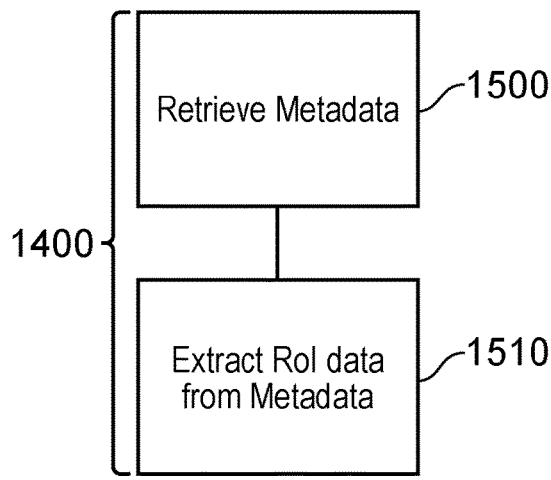
FIGS. 15a, 15b and 15c schematically illustrate region of interest identification methods.
Figure 15B:
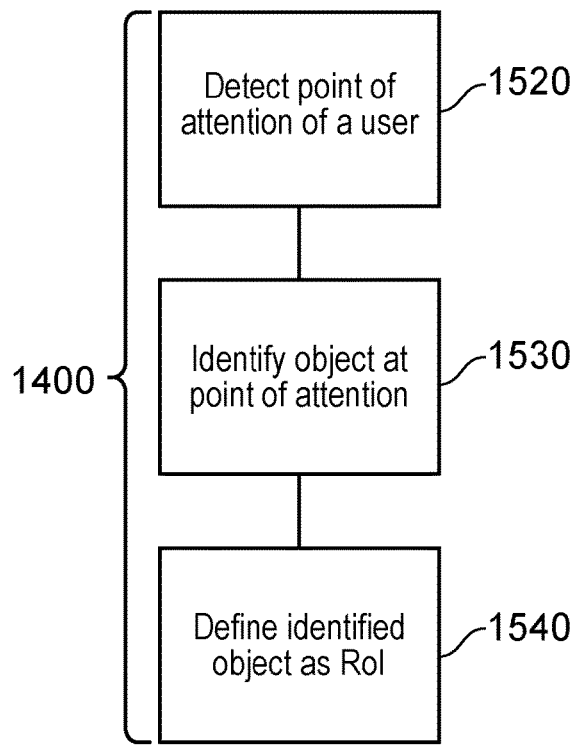
Figure 15C:
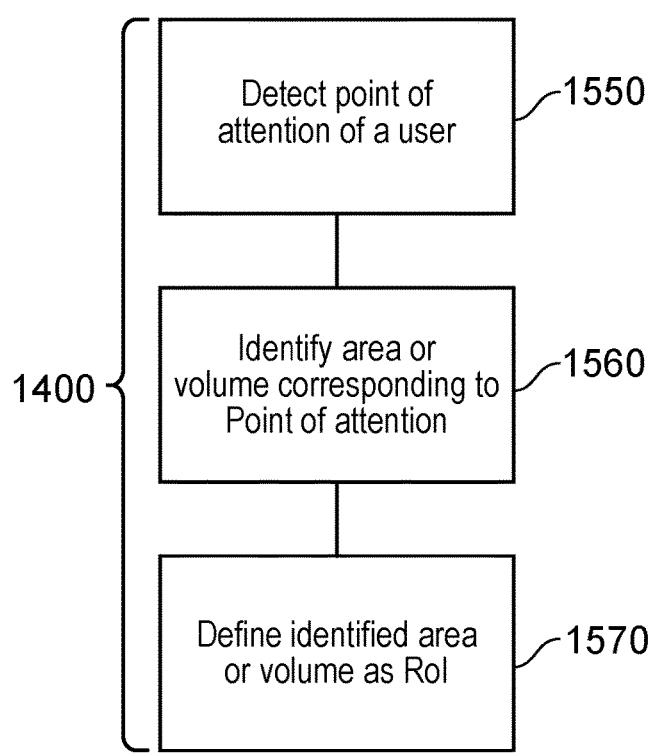

FIGS. 15*a*, 15*b* and 15*c* each schematically illustrate a method for identifying a region of interest (step 1400 of FIG. 14). FIG. 15*a* relates to a method in which contextual (or other) data about the region of interest is extracted from metadata, while FIGS. 15*b* and 15*c* relate to methods based upon detecting the user's gaze direction and point of attention.

FIG. 15*a* comprises a step 1500 of retrieving metadata from any appropriate source. For example, this metadata may be provided with the content, or obtained from the internet. This metadata (as described above) may identify specific objects or areas of a virtual scene that should be regarded as regions of interest. A step 1510 comprises extracting the region of interest data from this metadata.

FIG. 15*b* includes a step 1520 of detecting the point of attention of a user. This may be achieved using inward-facing cameras, for example, that monitor the positions and orientations of the users eyes and relate this to an area of the display screen. At a step 1530 an object is identified at this point of attention; this may be achieved by relating the display position of an object that the detected point of attention, for example. At a step 1540 the identified object is defined as the region of interest within the virtual scene.

Figure 16:
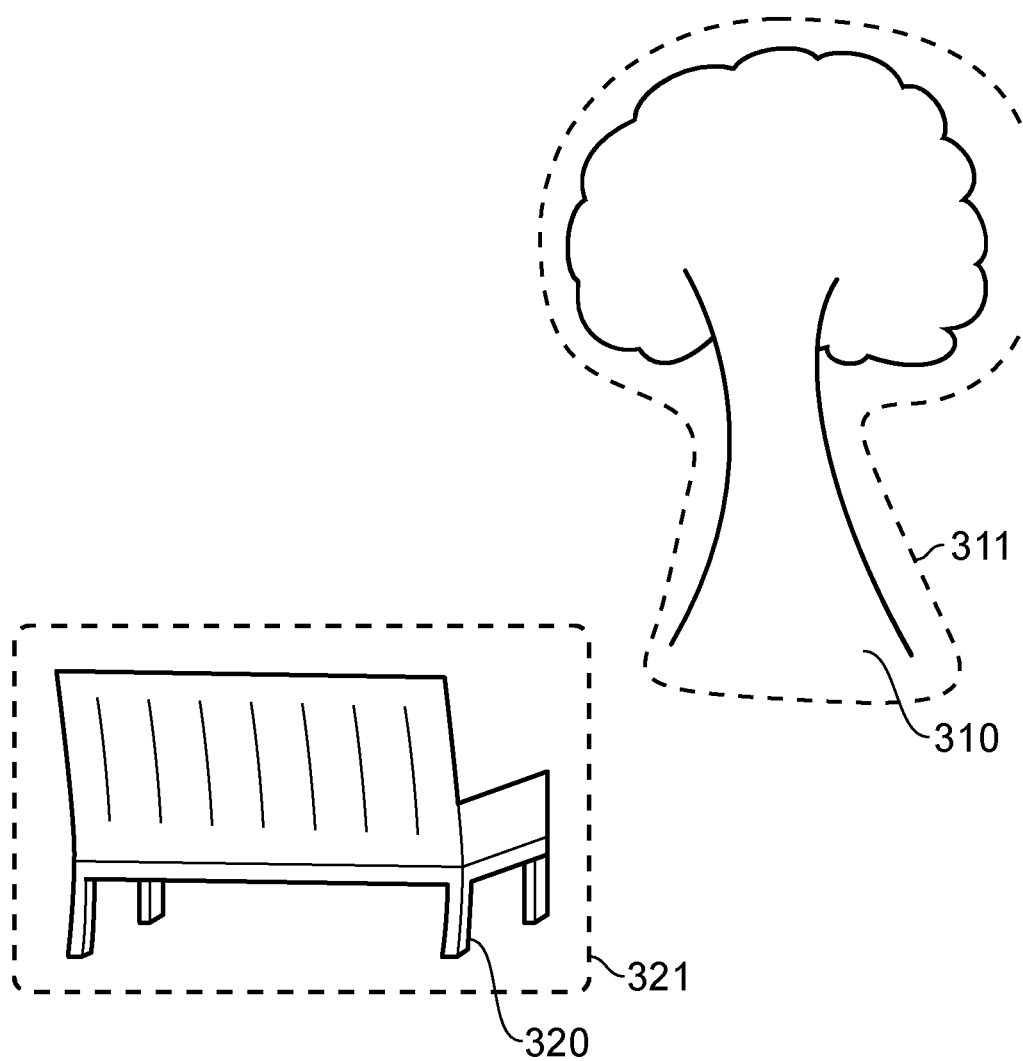
FIG. 16 schematically illustrates a virtual scene.

FIG. 16 schematically illustrates a portion of the virtual scene 300 with additional areas defined surrounding the objects 310 and 320. With respect to step 1530, this image illustrates a tolerance for selecting an object as the region of interest; this is advantageous in accounting for any errors in the gaze tracking, for example.

For example, if a user's gaze is determined to be anywhere within the region 311 or 321, then a link is made to the objects 310 or 320 respectively even if the user's gaze is not directly exactly towards these objects. The size of the areas 311 and 321 may be proportional to the size of the objects 310 and 321, or may be freely determined in any other manner (for example, defined in dependence upon the importance of the object in the context of the content being displayed, as defined in metadata).

FIG. 15c comprises a step 1550 of detecting the point of attention of a user, for example using gaze detection methods as described above. A step 1560 comprises identifying an area or a volume in a virtual scene that corresponds to the detected point of attention; this (similarly to step 1530 above) may be performed relating the position of the point of attention on the display to a location within the virtual scene being shown. A step 1570 comprises defining the identified area or volume as the region of interest; this area or volume is defined independently of an object, as this case is described with reference to FIG. 15b.

Instead, an area or volume is defined in one or more of any number of suitable methods. For example, a fixed size area or volume may be used that is dependent upon the size of the point of attention of the user—this may be dependent on factors such as the distance between the user's eyes and the display. Alternatively, or in addition, the area or volume may be defined in dependence upon available bandwidth and/or processing capabilities. This means that lower-power/-bandwidth systems may utilise a smaller area or volume.

In another example, an area or volume may be identified by considering the depth of areas in the image; for example, an area or volume may be defined so as to encompass the point of attention and any nearby parts of the virtual scene that have the same or a similar depth. The threshold distance from the point of attention and threshold depth difference may be selected freely by the skilled person, so as to acquire a suitable viewing experience.

FIGS. 17a and 17b schematically illustrate steps corresponding to step 1410 of FIG. 14. FIG. 17a relates to a method in which meshes and textures are selected and used to generate an image for display, while FIG. 17b relates to a method in which portions of two or more existing images are used to generate an image for display.

FIG. 17a comprises a step 1700 of selecting a mesh corresponding to an object to be displayed, and a step 1710 of selecting a texture associated with the selected mesh. Each of these selections is made in dependence upon whether the object appears in the region of interest; in addition to this, the selection may depend on how far (in a depth direction or other) the object is from the region of interest. The textures available for selection are dependent upon the object, however the selection may be limited further if each texture is only associated with a mesh of a particular level of quality. Finally, a step 1720 comprises rendering an image using the selected mesh and texture combination.

FIG. 17b comprises a step 1730 of identifying images corresponding to the scene to be displayed, such that each corresponding image (each having a particular quality) is identified. A step 1740 comprises identifying an area of the highest-resolution image corresponding to the region of interest, or at least the highest-resolution image that is to be used in generating an image for display. In some embodiments, it may not be appropriate to use the highest-quality image; for example, if a user has a low-quality display apparatus (and as a result cannot make use of the highest-quality image) or if data bandwidth is limited or the like.

A step 1750 comprises identifying other image areas in the other, lower-resolution image (or images) corresponding to the other parts of the scene. The image in which these areas are identified may be dependent upon their distance (depth or otherwise) from the region of interest. Finally, a step 1760 comprises combining each of the identified image areas into an image for display. This may be achieved using any form of image combining method, such as an image stitching software.

It will be appreciated that embodiments of the present invention may be implemented in hardware, programmable hardware, software-controlled data processing arrangements or combinations of these. It will also be appreciated that computer software or firmware used in such embodiments, and providing media for providing such software or firmware (such as storage media, for example a machine-readable non-transitory storage medium such as a magnetic or optical disc or a flash memory) are considered to represent embodiments of the present invention.

It will also be apparent that numerous modifications and variations of the present disclosure are possible in light of the above teachings. It is therefore to be understood that within the scope of the appended claims, the disclosure may be practised otherwise than as specifically described herein.

The invention claimed is:

1. An image generation system for generating 3D images, the system comprising:
   a region of interest identifying unit operable to identify a region of interest within a piece of content, the piece of content comprising one or more objects and the region of interest includes at least one of the one or more objects; and
   an image generation unit operable to generate an image representing the piece of content for display comprising one or more of the one or more objects and the at least one of the one or more objects, such that:
   (i) objects among the one or more of the one or more objects that are at a different visual depth to the region of interest, that includes the at least one of the one or more objects, are present in the generated image at least one of at a lower image quality and at a lower rendering quality, and
   (ii) a quality of the one or more of the one or more objects is varied in dependence upon a relationship between: (a) the one or more of the one or more objects, and (b) at least one of the one or more objects that is the region of interest, wherein the relationship is other than a spatial difference in visual depth,
   wherein the image generation unit is operable select one of a plurality of meshes specifically associated with the one or more of the one or more objects, each of the plurality of meshes being of a different quality, such that application of the selected one of the plurality of meshes to the one or more of the one or more objects in rendering the one or more of the one or more objects achieves the varying of the quality of the one or more of the one or more objects in dependence upon the relationship.

2. An image generation system according to claim 1, comprising an image display unit operable to display the generated images to a viewer.

3. An image generation system according to claim 2, wherein the image display unit is a head-mountable display device.

4. An image generation system according to claim 1, wherein the region of interest identifying unit is operable to identify the region of interest using contextual information for the piece of content.

5. An image generation system according to claim 1, wherein the region of interest identifying unit is operable to identify the region of interest using a detected point of attention of the user, the point of attention being obtained using eye tracking.

6. An image generation system according to claim 1, wherein the image generation unit is operable to vary the quality of the one or more of the one or more objects in the generated image such that the quality decreases with increasing depth difference from the region of interest, that includes the at least one of the one or more objects.

7. An image generation system according to claim 1, wherein the image generation unit is operable to select one of a plurality of available textures for use in rendering an object for display, the available textures each being of a different quality.

8. An image generation system according to claim 7, wherein the available textures corresponding to an object are each of a different resolution.

9. An image generation system according to claim 1, wherein the image generation unit is operable to generate an image by combining areas from one or more candidate images of different qualities.

10. An image generation method for generating 3D images, the method comprising:
   identifying a region of interest within a piece of content, the piece of content comprising one or more objects and the region of interest includes at least one of the one or more objects; and
   generating an image representing the piece of content for display comprising one or more of the one or more objects and the at least one of the one or more objects, such that:
   (i) objects among the one or more of the one or more objects that are at a different visual depth to the region of interest, that includes the at least one of the one or more objects, are present in the generated image at least one of at a lower image quality and at a lower rendering quality, and
   (ii) a quality of the one or more of the one or more objects is varied in dependence upon a relationship between: (a) the one or more of the one or more objects, and (b) at least one of the one or more objects that is the region of interest, wherein the relationship is other than a spatial difference in visual depth,
   wherein the generating includes selecting one of a plurality of meshes specifically associated with the one or more of the one or more objects, each of the plurality of meshes being of a different quality, such that application of the selected one of the plurality of meshes to the one or more of the one or more objects in rendering the one or more of the one or more objects achieves the varying of the quality of the one or more of the one or more objects in dependence upon the relationship.

11. A non-transitory machine-readable storage medium which stores computer software, which when executed by a computer, causes the computer to generate 3D images by carrying out actions, comprising:
   identifying a region of interest within a piece of content, the piece of content comprising one or more objects and the region of interest includes at least one of the one or more objects; and
   generating an image representing the piece of content for display comprising one or more of the one or more objects and the at least one of the one or more objects, such that:
   (i) objects among the one or more of the one or more objects that are at a different visual depth to the region of interest, that includes the at least one of the one or more objects, are present in the generated image at least one of at a lower image quality and at a lower rendering quality, and
   (ii) a quality of the one or more of the one or more objects is varied in dependence upon a relationship between: (a) the one or more of the one or more objects, and (b) at least one of the one or more objects that is the region of interest, wherein the relationship is other than a spatial difference in visual depth,
   wherein the generating includes selecting one of a plurality of meshes specifically associated with the one or more of the one or more objects, each of the plurality of meshes being of a different quality, such that application of the selected one of the plurality of meshes to the one or more of the one or more objects in rendering the one or more of the one or more objects achieves the varying of the quality of the one or more of the one or more objects in dependence upon the relationship.

* * * * *